United States Patent
Nose et al.

(10) Patent No.: US 6,916,946 B2
(45) Date of Patent: Jul. 12, 2005

(54) ACID HALIDE DERIVATIVES, THEIR PRODUCTION, AND PRODUCTION OF INDANONECARBOXYLIC ACID ESTERS USING THE SAME

(75) Inventors: Satoru Nose, Arai (JP); Kieko Sano, Himeji (JP); Syu-ichi Yamagiwa, Matsudo (JP); Takeshi Hamatani, Arai (JP)

(73) Assignee: Daicel Chemical Industries, Ltd., Sakai (JP)

( * ) Notice: Subject to any disclaimer, the term of this patent is extended or adjusted under 35 U.S.C. 154(b) by 0 days.

(21) Appl. No.: 10/797,185

(22) Filed: Mar. 11, 2004

(65) Prior Publication Data

US 2005/0043568 A1 Feb. 24, 2005

Related U.S. Application Data

(60) Provisional application No. 60/504,990, filed on Sep. 23, 2003.

(30) Foreign Application Priority Data

Aug. 20, 2003 (JP) ........................................ 2003-296830

(51) Int. Cl.$^7$ .......................... C07C 69/00; C07C 65/00
(52) U.S. Cl. ........................................ 560/139; 562/840
(58) Field of Search ........................... 560/139; 562/840

(56) References Cited

FOREIGN PATENT DOCUMENTS

| JP | 5-25164 | 2/1993 |
|---|---|---|
| JP | 2002-523392 | 7/2002 |
| WO | WO 91/05763 | 5/1991 |
| WO | WO 95/29171 | 11/1995 |
| WO | WO 00/10963 | 3/2000 |

OTHER PUBLICATIONS

Matveeva et al., Russian J. Org. Chem., vol. 38, No. 12, pp. 1769–1774 (2002).
Szabo et al., Synthesis, No. 6, pp. 565–566 (1987).
Flammang et al, Eur. J. Med. Chem., vol. 11, No. 1, pp. 1 83–87 (1976).
Ninomiya et al., Chem. Pharm. Bull., vol. 22, No. 8, pp. 1795–1799 (1974).
Kaiser et al., J. Med. Chem., vol. 13, No. 5, pp. 820–826 (1970).
Corey, J. Amer. Chem. Soc., vol. 74, pp. 5897–5905 (1952).

*Primary Examiner*—Cecilia J. Tsang
*Assistant Examiner*—Taylor Victor Oh
(74) *Attorney, Agent, or Firm*—Birch, Stewart, Kolasch & Birch, LLP

(57) ABSTRACT

Disclosed is a novel acid halide derivative represented by Formula (I):

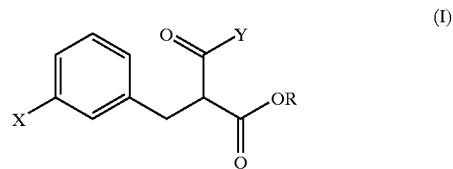

(I)

wherein X and Y may be the same or different and are each a halogen atom; and R is a lower alkyl group. By cyclizing the acid halide derivative of Formula (I) in the presence of a catalyst, an indanonecarboxylic acid ester represented by Formula (VI):

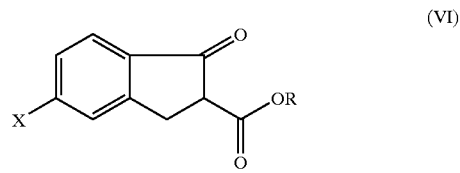

(VI)

wherein X and R are as defined above, is produced. Such indanonecarboxylic acid esters are useful as intermediates for insecticides.

6 Claims, No Drawings

ACID HALIDE DERIVATIVES, THEIR PRODUCTION, AND PRODUCTION OF INDANONECARBOXYLIC ACID ESTERS USING THE SAME

Applicant claims the right of priority under the provisions of 35 U.S.C. § 119 and 37 C.F.R. § 1.55(a) based on Application No(s). JP 2003-296830 and U.S. Ser. No. 60/504,990 filed in JAPAN and the United States on Aug. 20, 2003 and Sep. 23, 2003, respectively.

BACKGROUND OF THE INVENTION

1. Field of the Invention

The present invention relates to a novel acid halide derivative and its production, and the production of indanonecarboxylic acid ester using the acid halide derivative as a precursor. Such indanonecarboxylic acid esters are useful as intermediates for insecticides.

2. Description of the Related Art

Indanonecarboxylic acid esters are useful as intermediates for insecticides, and certain processes for producing the same have been known. For example, PCT International Publication No. WO 00/10963 discloses a process for producing an indanonecarboxylic acid ester, in which a halogenated anthranilic acid derivative is allowed to react with sodium nitrite or methyl nitrite to yield a diazonium salt, the diazonium salt is allowed to react with an acrylic acid derivative in the presence of a palladium-containing catalyst to yield a substituted cinnamic acid and an cinnamic ester, the substituted cinnamic acid and cinnamic ester are hydrogenated in the presence of a hydrogenation catalyst to yield a substituted arylpropionic acid, followed by cyclization (ring-closing) in the presence of a base to yield the target compound. However, this process requires the use of a diazonium salt which is difficult to handle in view of safety, inviting problems in production on an industrial scale.

PCT International Publication No. WO 95/29171 discloses a process for producing a substituted indanonecarboxylic acid ester, in which a para-substituted phenylacetyl halide and ethylene are subjected to Friedel-Crafts reaction to yield a substituted tetralone, the substituted tetralone is subjected to ring-opening reaction in the presence of a peroxycarboxylic acid to yield a substituted arylpropionic acid, the substituted arylpropionic acid is esterified, and the ester is subjected to cyclization (ring-closing) reaction in the presence of a base to yield the target compound. This process requires a peroxide for ring-opening of the substituted tetralone and invites problems in safety in production on an industrial scale.

Japanese Unexamined Patent Application Publication No. 05-25164 discloses a process for producing an indanonecarboxylic acid ester by esterifying a substituted indanone with, for example, dimethyl carbonate. As an example, a process for producing methyl indanonecarboxylate is disclosed, in which 5-chloroindanone is allowed to react with dimethyl carbonate in the presence of sodium hydride. However, this process achieves a yield of at most 50% and requires the use of sodium hydride which is dangerous and is difficult to handle.

Certain processes for producing malonic acid diester derivatives, malonic acid monoester derivatives, and acid halide derivatives have been known. For example, J. Med. Chem., 13, 1970, 820 discloses a process for producing diethyl 3-chlorobenzylmalonate by allowing diethyl malonate to react with m-chlorobenzyl chloride in the presence of sodium hydride. J. Amer. Chem. Soc., 74, 1952, 5897 discloses a process for producing a malonic monoester (half ester) by allowing diethyl phenylmalonate to react in the presence of potassium hydroxide in an aqueous ethanol solution. Chem. Pharm. Bull., 22, 1974, 1795 discloses a process for producing ethyl 2-chloroformyl-3-phenyl-propionate by allowing 3-phenyl-2-ethoxycarbonylpropionic acid to react with thionyl chloride. However, these processes have never been applied to the production of a 2-haloformyl-3-phenyl-propionic acid ester having a substituent on its aryl group.

SUMMARY OF THE INVENTION

Accordingly, an object of the present invention is to provide a novel acid halide derivative useful for the production of an indanonecarboxylic acid ester, and a production process thereof.

Another object of the present invention is to provide a process for safely producing an indanonecarboxylic acid ester in a high yield even on an industrial scale using the novel acid halide derivative.

After intensive investigations to achieve the above objects, the present inventors have found that an indanonecarboxylic acid ester can be safely prepared in a high yield from a novel acid halide derivative. The present invention has been accomplished based on these findings.

Specifically, the present invention provides an acid halide derivative represented by following Formula (I):

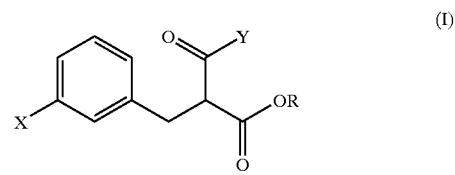

wherein X and Y may be the same or different and are each a halogen atom; and R is a lower alkyl group. An acid halide derivative wherein X and Y are chlorine atoms and R is a methyl group in Formula (I) is preferred.

The present invention further provides a process for producing an acid halide derivative represented by Formula (I), the process including the steps of:

(A) allowing a benzyl halide derivative represented by following Formula (II):

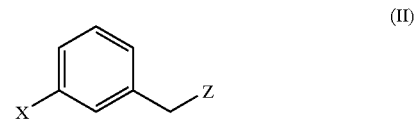

wherein X and Z may be the same or different and are each a halogen atom, to react with a malonic diester represented by following Formula (III):

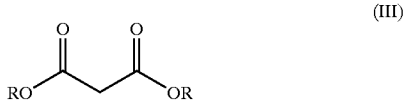

wherein R is a lower alkyl group, in the presence of a base to yield a malonic diester derivative represented by following Formula (IV):

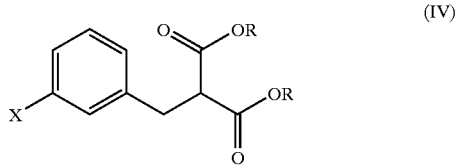

wherein X and R are as defined above;

(B) hydrolyzing the malonic diester derivative represented by Formula (IV) to yield a malonic monoester derivative represented by following Formula (V):

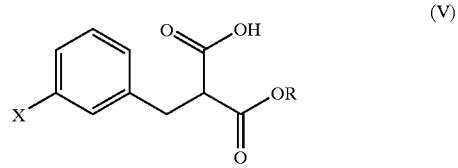

wherein X and R are as defined above; and (C) allowing the malonic monoester derivative represented by Formula (V) to react with a halogenating agent to yield the acid halide derivative represented by Formula (I).

In addition and advantageously, the present invention provides a process for producing an indanonecarboxylic acid ester represented by following Formula (VI):

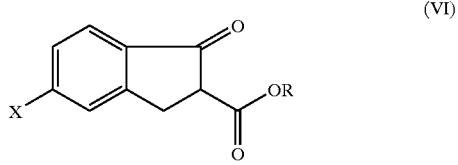

wherein X is a halogen atom; and R is a lower alkyl group, the process including the step of cyclizing the acid halide derivative represented by Formula (I) in the presence of a catalyst to yield the indanonecarboxylic acid ester represented by Formula (VI). The catalyst is preferably anhydrous aluminum chloride. In the process, an indanonecarboxylic acid ester of Formula (VI) where X is a chlorine atom and R is a methyl group is preferably used.

The present invention can yield novel acid halide derivatives in high yields. By using the novel acid halide derivatives, indanonecarboxylic acid esters can be safely produced in high yields on an industrial scale. The resulting indanonecarboxylic acid esters can be used as intermediates for insecticides.

Other and further objects, features and advantages of the present invention will be appear more fully from the following description.

DESCRIPTION OF THE PREFERRED EMBODIMENTS

In the acid halide derivatives represented by Formula (I), X and Y may be the same or different and are each a halogen atom, and R is a lower alkyl group.

The halogen atom includes fluorine atom, chlorine atom, bromine atom, and iodine atom, of which chlorine atom is preferred. Examples of the lower alkyl group are methyl group, ethyl group, n-propyl group, isopropyl group, n-butyl group, isobutyl group, sec-butyl group, t-butyl group, n-pentyl group, isopentyl group, sec-pentyl group, t-pentyl group, 2-methylbutyl group, n-hexyl group, 1-methylpentyl group, 2-methylpentyl group, 3-methylpentyl group, 4-methylpentyl group, 1-ethylbutyl group, 2-ethylbutyl group, 1,1-dimethylbutyl group, 2,2-dimethylbutyl group, 3,3-dimethylbutyl group, 1-ethyl-1-methylpropyl group, and other linear or branched $C_1$–$C_6$ alkyl groups. Among them, $C_1$–$C_4$ alkyl groups are preferred, of which methyl group is typically preferred.

A typical acid halide derivative is methyl 2-chloroformyl-3-(3-chlorophenyl)-propionate.

The process for producing an acid halide derivative according to the present invention includes the steps of (A) allowing a benzyl halide derivative of Formula (II) to react with a malonic diester of Formula (III) in the presence of a base to yield a malonic diester derivative of Formula (IV), (B) hydrolyzing the malonic diester derivative of Formula (IV) to yield a malonic monoester derivative of Formula (V), and (C) allowing the malonic monoester derivative of Formula (V) to react with a halogenating agent to yield an acid halide derivative of Formula (I).

In Step A, X and Z in the benzyl halide derivative of Formula (II) may be the same or different and are each a halogen atom. The halogen atom in Z includes those exemplified as the halogen atom in X in Formula (I). Preferred halogen atoms in Z are chlorine atom, bromine atom, and iodine atom, of which chlorine atom is typically preferred.

Examples of the substituents X and R in Formulae (III), (IV), and (V) are those mentioned above.

The base includes, but is not limited to, carbonates including carbonates of alkali metals, such as potassium hydrogencarbonate, sodium hydrogencarbonate, potassium carbonate, and sodium carbonate; hydroxides of alkali metals, such as sodium hydroxide and potassium hydroxide; hydroxides of alkaline earth metals, such as calcium hydroxide and magnesium hydroxide; phosphates including phosphates of alkali metals, such as sodium dihydrogenphosphate and potassium dihydrogenphosphate; carboxylates including carboxylates of alkali metals, such as sodium acetate and potassium acetate; organic bases such as triethylamine and pyridine; metal alkoxides including alkoxides of alkali metals, such as sodium methoxide and sodium ethoxide; and metal hydrides such as sodium hydride. Each of these bases can be used alone or in combination. Preferred examples of the base are hydroxides of alkali metals.

The amount of the malonic diester of Formula (III) is, for example, from about 0.1 to about 1000 moles, preferably from about 1.1 to about 100 moles, and more preferably from about 2 to about 10 moles per 1 mole of the benzyl halide derivative of Formula (II). To avoid the formation of by-products as a result of a reaction between 1 mole of the malonic diester and 2 moles of the benzyl halide derivative, the malonic diester is generally used in excess. After the completion of the reaction, unreacted malonic diester can be recovered and recycled. The amount of the base is generally from about 0.01 to about 100 gram equivalents, preferably from about 0.1 to 10 gram equivalents, more preferably from about 0.25 to about 4 gram equivalents, and especially preferably from about 0.9 to 1.5 gram equivalents per 1 mole of the benzyl halide derivative.

The reaction can be performed in the presence of a reaction aid. Examples of the reaction aid are sodium bromide, potassium bromide, sodium iodide, potassium iodide, and other alkali metal halides; 12-crown-4,15-crown-5,18-crown-6, and other crown ethers; quaternary alkyls, aryl-substituted ammonium, and other phase transfer catalysts.

The reaction is performed in the presence of, or in the absence of, a solvent. The solvent is not specifically limited, as long as it is inert to reaction components and is separable from products. Examples of such solvents are acetone, ethyl methyl ketone, and other ketones; tetrahydrofuran, dioxane, and other ethers; acetonitrile and other nitrites; dimethyl sulfoxide and other sulfoxides; sulfolane and other sulfones; ethyl acetate and other esters; dimethylformamide, dimethylacetamide, and other amides; methanol, ethanol, t-butanol, and other alcohols; pentane, hexane, petroleum ether, and other aliphatic or alicyclic hydrocarbons; benzene, toluene, xylene, and other aromatic hydrocarbons; methylene chloride, chloroform, bromoform, chlorobenzene, bromobenzene, and other halogen-containing compounds; polyethylene glycol, silicone oil, other high-boiling solvents, and other organic solvents; as well as water. Each of these solvents can be used alone or in combination. The amount of the solvent, if used, is not specifically limited, as long as reaction components can be sufficiently dispersed therein, and its upper limit may be set in view of economical factors.

A reaction temperature is not specifically limited, as long as it is equal to or higher than the melting point of the system, and is, for example, from about −30° C. to about +300° C., and preferably from about −10° C. to about +200° C. The reaction can efficiently proceed even under mild conditions such as a temperature around room temperature (5° C. to 40° C.).

The reaction can be performed at normal atmospheric pressure, under reduced pressure or under a pressure (under a load) but is generally performed at normal atmospheric pressure. The reaction can be conducted in a system such as batch system, semi-batch system or continuous system.

The malonic diester derivative prepared in Step A may be isolated from the reaction mixture, but the reaction mixture including the product as intact or after concentration can be subjected to Step B as a raw material.

The amount of water for use in the hydrolysis reaction in Step B can be set according to, for example, the type of the malonic diester derivative, the reaction mode, and the reaction rate and is, for example, from about 0.1 to about 1000000 moles, preferably from about 0.5 to about 1000 moles, and more preferably from about 0.8 to about 100 moles per 1 mole of the malonic diester derivative.

A reaction aid can be used in the hydrolysis reaction for accelerating the reaction. As the reaction aid, an acid or base is used. Examples of the acid are sulfuric acid, hydrochloric acid, phosphoric acid, nitric acid, and other inorganic acids, carboxylic acids (e.g., acetic acid, propionic acid, and other $C_1$–$C_{10}$ saturated or unsaturated mono- or poly-carboxylic acids), sulfonic acids (e.g., methanesulfonic acid, ethanesulfonic acid, and other $C_1$–$C_6$ alkanesulfonic acids; benzenesulfonic acid, p-toluenesulfonic acid, and other aromatic sulfonic acids), halogenated organic acids (e.g., trifluoroacetic acid, and other halogenated carboxylic acids; trifluoromethanesulfonic acid, and other halogenated alkanesulfonic acids), and other organic acids; sulfates (e.g., calcium sulfate), metal oxides (e.g., $SiO_2$ and $Al_2O_3$), zeolites (e.g., zeolite Y, zeolite X, and zeolite A having an acidic OH), ion-exchange resins (e.g., H-type and other cation-exchange resins), and other solid acids. Examples of the base for use herein are those mentioned as the base in Step A. Preferred examples of the base are hydroxides of alkali metals. Each of these reaction aids can be used alone or in combination.

The amount of the reaction aid is not specifically limited and is, for example, from about 0.01 to about 5 moles, preferably from about 0.1 to about 2 moles, and more preferably from about 0.8 to about 1.2 moles per 1 mole of the malonic diester derivative. The reaction can also be accelerated, for example, by heating when the reaction aid is not used.

The reaction is performed in the presence of, or in the absence of, a solvent. Examples of the solvent for use herein are the organic solvents exemplified as the solvents in Step A. Each of the solvents can be used alone or in combination. Preferred solvents are alcohols, of which alcohols each having the same subsistent as the substituent R in the malonic diester derivative are typically preferred to avoid halogen exchange reactions.

A reaction temperature is not specifically limited, as long as it is equal to or higher than the melting point of, and equal to or lower than the boiling point of the system, and is, for example, from about −30° C. to about +300° C., and preferably from about −10° C. to about +200° C. The reaction can efficiently proceed even under mild conditions such as a temperature around room temperature (5° C. to 40° C.).

The reaction can be performed at normal atmospheric pressure, under reduced pressure or under a pressure (under a load) but is generally performed at normal atmospheric pressure. The reaction can be conducted in a system such as batch system, semi-batch system or continuous system.

The malonic monoester derivative prepared in Step B may be isolated from the reaction mixture, but the reaction mixture including the product as intact or after concentration can be subjected to Step C as a raw material.

The halogenating agent for use in Step C includes, but is not limited to, potassium hydrogenfluoride, potassium fluoride, and other fluorinating agents; thionyl chloride, oxalyl chloride, phosphorus pentachloride, phosphorus oxychloride, and other chlorinating agents; thionyl bromide, phosphorus tribromide, phosphorus pentabromide, phosphorus oxybromide, and other brominating agents; phosphorus triiodide, and other iodinating agents. The substituent Y in Formula (I) is a halogen atom corresponding to the halogenating agent used.

The amount of the halogenating agent is not specifically limited and is, for example, a large excess amount when the reaction is performed in the absence of a solvent and is about 1 mole or more, and preferably from about 1 to about 4 moles per 1 mole of the malonic monoester derivative when the reaction is performed in the presence of a solvent.

The reaction may be performed in the presence of a reaction aid. Examples of the reaction aid are zinc chloride, pyridine, iodine, triethylamine, dimethylformamide, and hexamethylphosphoramide (HMPA).

The reaction is performed in the presence of, or in the absence of, a solvent. The solvent is not specifically limited, as long as it is inert to reaction components and is separable from products. Examples of such solvents are tetrahydrofuran, dioxane, and other ethers; dimethyl sulfoxide, and other sulfoxides; dimethylformamide, and other amides; pentane, hexane, petroleum ether, and other aliphatic or alicyclic hydrocarbons; benzene, toluene, xylene, and other aromatic hydrocarbons; methylene chloride, chloroform, bromoform, chlorobenzene, bromobenzene, and other halogen-containing compounds. Each of these solvents can be used alone or in combination. The amount of the solvent, if used, is not specifically limited, as long as the reaction components can be sufficiently dispersed therein, and its upper limit may be set in view of economical factors.

A reaction temperature is not specifically limited, as long as it is equal to or higher than the melting point of, and equal to or lower than the boiling point of the system, and is, for example, from about $-30°$ C. to about $+300°$ C., preferably from about $-10°$ C. to about $+200°$ C., and more preferably from about $+10°$ C. to about $+100°$ C.

The reaction can be performed at normal atmospheric pressure, under reduced pressure or under a pressure (under a load) but is generally performed at normal atmospheric pressure. The reaction can be conducted in a system such as batch system, semi-batch system or continuous system.

According to the above process, the benzyl halide derivative of Formula (II) reacts with the malonic diester of Formula (III) to yield the malonic diester derivative of Formula (IV), the malonic diester derivative of Formula (IV) is hydrolyzed to yield the malonic monoester derivative of Formula (V), the malonic monoester derivative of Formula (V) reacts with the halogenating agent to yield the corresponding acid halide derivative of Formula (I). After the completion of the reaction, reaction product(s) can be separated and purified by separation means such as filtration, concentration, distillation, extraction, ion exchange, electrodialysis, crystallization, recrystallization, adsorption, membrane separation, centrifugation, chromatography (e.g., column chromatography) and combinations of these means.

Production Process of Indanonecarboxylic Acid Esters

The indanonecarboxylic acid esters of Formula (IV) can be produced by a process in which the acid halide derivative of Formula (I) is cyclized in the presence of a catalyst. The substituents X and R in the indanonecarboxylic acid esters of Formula (VI) are the same as above.

The acid halide derivative of Formula (I) can be one produced by the process of the present invention. The acid halide derivative can be separated after the completion of the reaction in Step C, or the reaction mixture without separation and purification can be used in this process as intact or after concentration.

Examples of the catalyst are anhydrous aluminum chloride, anhydrous aluminum bromide, anhydrous iron chloride, titanium tetrachloride, tin tetrachloride, zinc chloride, boron trifluoride diethyl ether complex, anhydrous boron trioxide, concentrated sulfuric acid, and other Lewis acid catalysts that can be generally used in Friedel-Crafts reactions, of which anhydrous aluminum chloride is preferred.

The amount of the catalyst is, for example, from about 1 to about 50 moles, and preferably from about 2 to about 10 moles per 1 mole of the acid halide derivative.

The reaction is performed in the presence of, or in the absence of, a solvent. The solvent is not specifically limited, as long as it is inert to reaction components and is separable from products. Examples of such solvents are methylene chloride, chloroform, 1,2-dichloroethane, carbon tetrachloride, bromoform, chlorobenzene, nitromethane, nitrobenzene, carbon disulfide, and other solvents generally used in Friedel-Crafts reactions. Each of these solvents can be used alone or in combination. The amount of the solvent, if used, is not specifically limited, as long as reaction components can be sufficiently dispersed therein, and its upper limit may be set in view of economical factors.

A reaction temperature is not specifically limited, as long as it is equal to or higher than the melting point of, and equal to or lower than the boiling point of the system, and is, for example, from about $-30°$ C. to about $+300°$ C., and preferably from about $-10°$ C. to about $+100°$ C.

The reaction can be performed at normal atmospheric pressure, under reduced pressure or under a pressure (under a load) but is generally performed at normal atmospheric pressure. The reaction can be conducted in a system such as batch system, semi-batch system or continuous system.

According to the process, the acid halide derivative of Formula (I) is cyclized (ring-closed) as a result of the reaction in the presence of the catalyst and thereby yields a corresponding indanonecarboxylic acid ester of Formula (VI). After the completion of the reaction, reaction product (s) can be separated and purified by separation means such as filtration, concentration, distillation, extraction, ion exchange, electrodialysis, crystallization, recrystallization, adsorption, membrane separation, centrifugation, chromatography (e.g., column chromatography) and combinations of these means.

EXAMPLES

The present invention will be illustrated in further detail with reference to several examples below, which are not intended to limit the scope of the invention. Products were quantitatively determined by high-performance liquid chromatography.

NMR spectra were determined at 270 MHz ($^1$H-NMR) with tetramethylsilane (TMS) as internal control using apparatus JNM-EX270 (trade name, available from JEOL Ltd., Japan).

Example 1

Production of methyl 2-chloroformyl-3-(3'-chlorophenyl)-propionate

[Step A: Production of dimethyl 3-chlorobenzylmalonate]

In 41.8 g of dimethylacetamide were dissolved 6.6 g of m-chlorobenzyl chloride and 27.6 g of dimethyl malonate, followed by addition of 2.5 g of sodium hydroxide. The mixture was stirred at room temperature for 6 hours, was cooled to 5° C. or below and was adjusted to pH 3.5 using 1.7% by weight hydrochloric acid. The mixture was diluted with 36.0 g of water and was extracted with 37.0 g of toluene. The toluene layer was washed with two portions of 36.0 g of water, and toluene and unreacted dimethyl malonate were removed under reduced pressure to yield 9.7 g of a concentrated residue. The residue contained 96% by weight of dimethyl 3-chlorobenzylmalonate (yield: 9.3 g, 95%).

[Step B: Production of 3-(3'-chlorophenyl)-2-methoxycarbonylpropionic acid]

A total of 9.5 g of the concentrated residue containing dimethyl 3-chlorobenzylmalonate prepared in Step A was dissolved in 118.6 g of methanol, followed by dropwise addition of 148.0 g of 1% by weight aqueous sodium hydroxide solution. The mixture was stirred at room temperature for 3 hours, was cooled to 5° C. or below and was adjusted to pH 2.5 using 1.7% by weight hydrochloric acid. The product was extracted with three portions of 102.3 g of toluene, from which toluene was removed under reduced pressure to yield 8.7 g of a concentrated residue. The residue contained 95% by weight of 3-(3'-chlorophenyl)-2-methoxycarbonylpropionic acid (yield: 8.3 g, 92%).

[Step C: Production of methyl 2-chloroformyl-3-(3'-chlorophenyl)-propionate]

A total of 8.0 g of the concentrated residue containing 3-(3'-chlorophenyl)-2-methoxycarbonylpropionic acid prepared in Step B was dissolved in 32.8 g of 1,2-dichloroethane in an atmosphere of nitrogen gas, followed by addition of 11.8 g of thionyl chloride and 0.05 g of dimethylformamide. The mixture was stirred at 40° C. for 7 hours, from which 1,2-dichloroethane and unreacted thionyl chloride were removed under reduced pressure to yield 7.98 g of methyl 2-chloroformyl-3-(3'-chlorophenyl)-propionate. The NMR spectral data of this compound are shown below.

[Spectral data of methyl 2-chloroformyl-3-(3'-chlorophenyl)-propionate]

$^1$H-NMR (CDCl$_3$) ppm: 3.27 (d, 2H, ClC$_6$H$_4$-C$\underline{H}_2$—CH), 3.78 (s, 3H, —COOC$\underline{H}_3$), 4.07 (t, 1H, ClC$_6$H$_4$—CH$_2$—C$\underline{H}$), 7.07–7.26 (m, 4H, ClC$_6$$\underline{H}_4$—)

Example 2

Production of methyl 5-chloro-1-oxo-2,3-dihydroindene-2-carboxylate (i.e., 5-chloro-2-methoxycarbonylindan-1-one)

A total of 9.0 g of anhydrous aluminum chloride was suspended in 151.3 g of 1,2-dichloroethane by stirring in an atmosphere of nitrogen gas and was cooled to 0° C. To the cooled suspension was added dropwise a mixture of 7.98 g of methyl 2-chloroformyl-3-(3'-chlorophenyl)-propionate prepared in Example 1 and 151.3 g of 1,2-dichloroethane held at 5° C. or below, followed by stirring under the same conditions for 2 hours. The reaction mixture was added dropwise to 53.6 g of 1.7% by weight hydrochloric acid cooled at 5° C. or below, followed by stirring under the same conditions for 1 hour. The 1,2-dichloroethane layer was separated from the aqueous layer, and the product was further extracted from the aqueous layer with two portions of 15.1 g of 1,2-dichloroethane. The 1,2-dichloroethane layers were collected and were washed with 33.0 g of water, from which 1,2-dichloroethane was removed under reduced pressure. The concentrated residue was purified by silica gel column chromatography [mobile phase: hexane/ethyl acetate=4/1 (by volume)] to yield 5.21 g of methyl 5-chloro-1-oxo-2,3-dihydroindene-2-carboxylate as a beige solid in a yield of 70% on the basis of 3-(3'-chlorophenyl)-2-methoxycarbonylpropionic acid.

INDUSTRIAL APPLICABILITY

The present invention can efficiently produce indanonecarboxylic acid esters without any safety problems even on an industrial scale. The indanonecarboxylic acid esters are useful as intermediates for insecticides.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An acid halide represented by following Formula (I):

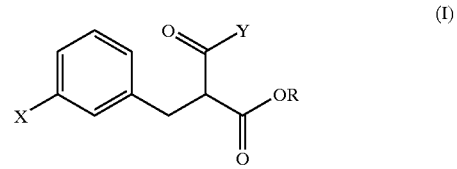

wherein X and Y may be the same or different and are each a halogen atom; and R is a lower alkyl group.

2. The acid halide according to claim 1, wherein X and Y are chlorine atoms and R is a methyl group in Formula (I).

3. A process for producing an acid halide represented by following Formula (I):

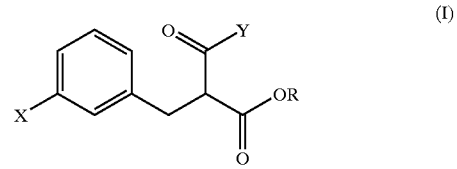

wherein X and Y may be the same or different and are each a halogen atom; and R is a lower alkyl group, the process comprising the steps of:

(A) allowing a benzyl halide represented by following Formula (II):

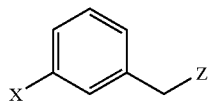
(II)

wherein X is as defined above; Z is a halogen atom, and X and Z may be the same or different, to react with a malonic diester represented by following Formula (III):

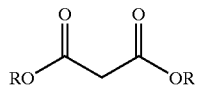
(III)

wherein R is a lower alkyl group, in the presence of a base to yield a malonic diester represented by following Formula (IV):

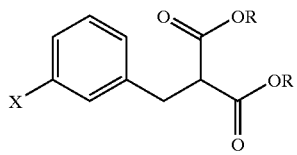
(IV)

wherein X and R are as defined above;

(B) hydrolyzing the malonic diester represented by Formula (IV) to yield a malonic monoester represented by following Formula (V):

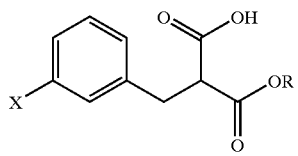
(V)

wherein X and R are as defined above; and (C) allowing the malonic monoester represented by Formula (V) to react with a halogenating agent to yield the acid halide represented by Formula (I).

4. A process for producing an indanonecarboxylic acid ester represented by following Formula (VI):

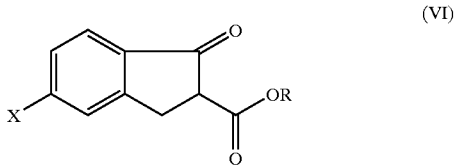
(VI)

wherein X is a halogen atom; and R is a lower alkyl group, the process comprising the step of cyclizing an acid halide represented by following Formula (I):

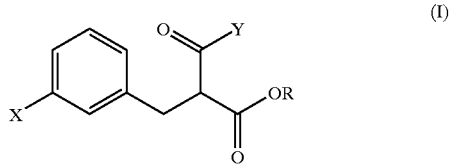
(I)

wherein X and R are as defined above; Y is a halogen atom, and X and Y may be the same or different, in the presence of a Lewis acid catalyst to yield the indanonecarboxylic acid ester represented by Formula (VI).

5. The process according to claim 4, wherein the catalyst is anhydrous aluminum chloride.

6. The process according to claim 4 or 5, wherein X is a chlorine atom and R is a methyl group.

* * * * *